United States Patent
Windhab et al.

(10) Patent No.: US 8,522,616 B2
(45) Date of Patent: Sep. 3, 2013

(54) METHOD FOR THE IN-LINE MEASUREMENT OF THE SETTING, CONTRACTION AND WALL RELEASE BEHAVIOUR OF CONFECTIONERY/CHOCOLATE PRODUCTS WHICH HAVE BEEN POURED INTO MOULDS DURING PRODUCTION, AND APPARATUS FOR CARRYING OUT THIS METHOD

(75) Inventors: Erich J. Windhab, Hemishofen (CH); Yvonne Mehrle, Wadgassen (DE); Bruno Pfister, Hüentwangen (CH)

(73) Assignee: ETH Zurich, Zurich (CH)

( * ) Notice: Subject to any disclaimer, the term of this patent is extended or adjusted under 35 U.S.C. 154(b) by 219 days.

(21) Appl. No.: 12/992,979

(22) PCT Filed: May 15, 2009

(86) PCT No.: PCT/EP2009/003484
§ 371 (c)(1),
(2), (4) Date: Apr. 5, 2011

(87) PCT Pub. No.: WO2009/138246
PCT Pub. Date: Nov. 19, 2009

(65) Prior Publication Data
US 2011/0174077 A1    Jul. 21, 2011

(30) Foreign Application Priority Data
May 16, 2008   (DE) .................. 10 2008 024 050

(51) Int. Cl.
*G01N 29/02*   (2006.01)

(52) U.S. Cl.
USPC .................................. 73/579; 73/597; 73/599

(58) Field of Classification Search
USPC ............................ 73/579, 573, 597, 599, 602
See application file for complete search history.

(56) References Cited

U.S. PATENT DOCUMENTS 6,655,213 B1 * 12/2003 Reinhardt et al. .............. 73/597
7,415,883 B2 * 8/2008 Kaplan .......................... 73/703

(Continued)

FOREIGN PATENT DOCUMENTS
DE   10 2008 024 050 B4   12/2009

(Continued)

OTHER PUBLICATIONS

Raffaella Saggin et al., Measurement of solid fat content by ultrasonic reflectance in model systems and chocolate, Food Research International 35, 2002. Elsevier Science Ltd.
Malcolm J. W. Povey, Ultrasonics of food, Contemporary Physics, 1998, pp. 467-478, vol. 39, No. 6.

*Primary Examiner* — J M Saint Surin
(74) *Attorney, Agent, or Firm* — Antonelli, Terry, Stout & Kraus, LLP.

(57) ABSTRACT

The invention relates to a method and a device for detecting the solidification behavior of pourable and solidifying masses and/or masses that are to be solidified, in particular of chocolate-type masses, as well as their separation behavior from their delimiting walls that are in contact with these masses, specifically molds. Solutions are offered regarding how to achieve the optimized point in time for demolding and for achieving optimized product surface quality taking into account process orders of magnitude such as cooling temperature, cooling speed and conveyor belt speed.

20 Claims, 5 Drawing Sheets

(56) References Cited

U.S. PATENT DOCUMENTS

Figure 1:
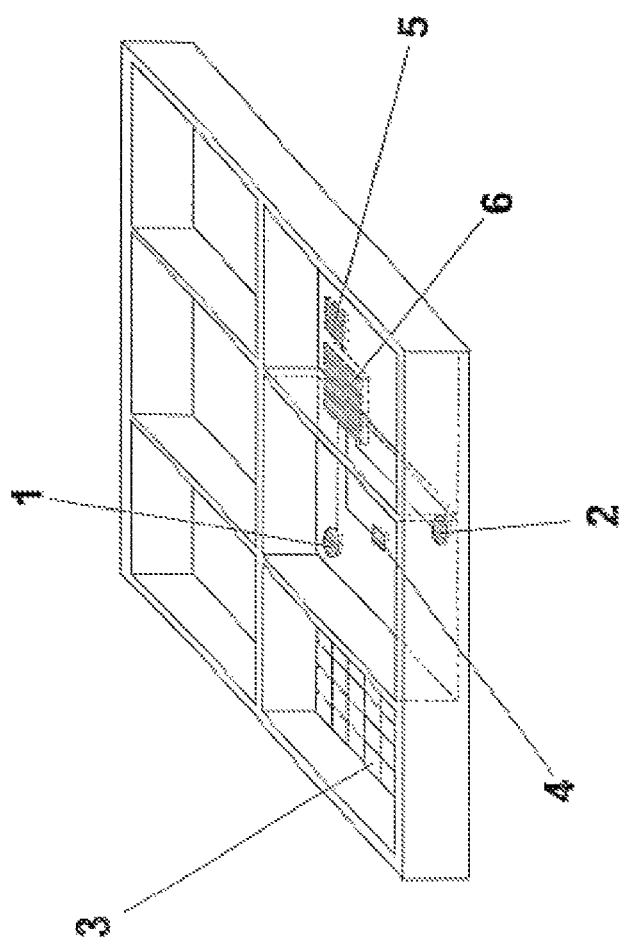

| | | | |
|---|---|---|---|
| 8,215,172 B2 * | 7/2012 | Lootens et al. | 73/596 |
| 2003/0051535 A1 | 3/2003 | Coupland et al. | |
| 2006/0123914 A1 | 6/2006 | Pena et al. | |
| 2009/0217758 A1 * | 9/2009 | Loeser et al. | 73/573 |

FOREIGN PATENT DOCUMENTS

| | | | |
|---|---|---|---|
| EP | 0 577 511 A1 | | 1/1994 |
| EP | 2140766 | * | 7/2008 |
| FR | 2 656 425 A1 | | 6/1991 |
| JP | 407008170 | * | 1/1995 |

* cited by examiner

METHOD FOR THE IN-LINE MEASUREMENT OF THE SETTING, CONTRACTION AND WALL RELEASE BEHAVIOUR OF CONFECTIONERY/CHOCOLATE PRODUCTS WHICH HAVE BEEN POURED INTO MOULDS DURING PRODUCTION, AND APPARATUS FOR CARRYING OUT THIS METHOD

The invention relates to a method for the in-line measurement of the solidification, contraction and wall separation behaviors of confectionary/chocolate products that are poured into molds during their production.

The invention relates furthermore to a device for the implementation of this method.

When producing individual pieces of confectionary/chocolate products the still-liquid chocolate or filling mass is poured into molds and subjected to a cooling treatment during the further course of the production process. The filled molds are cooled in a cooling chamber (in batches) or in a cooling tunnel (continuous). During this process, the beginning solidifying crystallization of the fat component, which normally constitutes the continuous initially fluid suspension phase, results in a volume contraction that depends in terms of its characteristics on the fat content (i), type of fat/fat mixture, (ii) the type and degree of any possible pre-crystallization (iii) and the product to be separated from the mold surrounding it. For a flawless and homogenously glowing surface of the chocolate product it is important that the chocolate has separated evenly and completely from the walls of the mold before it is removed from the mold in order to prevent adhesion/cooling spots or to leave product behind that sticks to the walls of the mold.

To date, the time at which the product can be removed from the mold without detriment to its quality has been determined empirically, by trial and error. This results in tedious adjustment periods and product rejects until the proper adjustment of the cooling component of the production facility has been found. Changes in the recipe of the product, in raw materials, mold sizes and materials, room/environmental temperatures, cooling temperature, cooling air speed and dwelling time in the cooling line are orders of magnitude that have a determinative influence on the kinetics of the cooling, solidification and wall separation processes.

With the innovative in-line measurement device according to the invention it is now possible for the first time to detect the progression of the cooling (i), solidification (ii) and product separation processes from the walls of the mold (iii) precisely and in-line. For the first time, this creates the possibility of a targeted optimized design of a cooling process taking into account all of the previously mentioned related parameters. The optimization criteria are: (i) the exact determination of the demolding time, (ii) the best possible abbreviation of said time, while (iii) ensuring an optimal, optically homogenous, glowing product surfaces. In contrast to the prior art, which does not allow for the in-line detection of the solidification and wall separation behaviors, the device and method according to the invention mean (a) fewer production errors, (b) improved consistency in product quality and (c) a longer mold life, which results in the possibility of visible cost reductions and expanded market potential.

Literature and patent searches have revealed that no in-line measuring device for the detection of the solidification, contraction and mold separation behaviors of chocolates or chocolate-type products has been described to date. The chocolate-making industry at times utilizes optical measuring devices that sort out products not meeting the desired surface quality criteria, after the pieces have been removed from their molds. Based on the number of sorted out pieces per time unit, for example, the throughput is changed by the speed of the mold conveyor belt.

In the area of injection molding engineering the time when the component has separated from the wall is determined by pressure measurements at one or two given wall locations inside the mold. This method only determines the point in time of separation at one (or two) location(s). Moreover, the surface of the pressure sensor is comprised of a different material than the mold itself, which means the separation behavior from the pressure sensor surface is not representative for the separation behavior of the mold wall material. For confectionary products it is, moreover, also undesirable if instead of a uniformly glowing product surface imprints of sensor installations are visible on the product surface.

Different industries utilize ultrasound technology as a basis for measurement techniques that are used in the detection of material structures. For example, the ultrasonic reflection characteristics relative to materials of differing density and/or different sound velocities are utilized for the detection of material errors, including in metallic materials /1-3/. In the construction industry ultrasonic measuring techniques are used to test concrete walls for contraction cavities (enclosed air cavities). In medical engineering tissue structures of different densities are visualized for diagnostic purposes /4/. In the case of moving media/objects, ultrasonic motion detection processes (Doppler) are able to detect velocity fields and/or volume flows /5/. Combining ultrasonic motion detection and pressure measuring techniques allows for the in-line measurements of complex rheological properties /6, 7/.

FR 2 656 425 A1 discloses a method and a device for the destruction-free examination of concrete elements; in this instance, when testing pre-stressed concrete it is of special significance to know the solidity that the concrete has achieved at the time the reinforcements are dismantled following the drying cycle. In fact, this will influence the adhesion of steel and concrete and therefore the definitive properties of the pre-stressed element. To this end, ultrasonic converters are used inside the mold; and whereby the ultrasonic converters are disposed on a wall of the mold that is opposite of another wall that has at least one converter receiver attached to it. In addition, an electronic unit is employed that is connected to the individual converters and intended to establish the propagation times of at least one wave propagating in the concrete between a converter-transmitter and at least one converter-receiver. In addition, a programmable computer is available that is connected to the electronic unit at the input side and with a display device at the output side; its purpose is the processing of the aforementioned propagation times of the waves in order to yield continuous data regarding the development of at least one feature of the concrete element. The device per se comprises a mold into which the fresh concrete is poured that is to be form-vibrated. The mold is equipped with the ultrasonic converters having at least one transmitter that is fastened to one of the vertical walls of the mold, while several receivers are arranged on the opposite wall of the mold. The mold per de is connected to several heating devices that are intended to heat the concrete in order to accelerate concrete hardening. Overall, the measured values are to be used for a drying analysis of the concrete during the drying cycle in order to thereby optimize the drying cycles. The goal is to achieve fast, high-level hardening of the concrete.

The essay by R. Saggin, et. aL, "Measurement of solid fat content by ultrasonic reflectance in model systems and chocolate", Food Research International 35, 15 (2002), pp. 999-1005 deals with controlling content materials during the production of chocolate products by measuring the fat content (solid fat content—SFC). Measuring the SFC is not suitable for determining the demolding behavior of confectionary/chocolate products.

US 2006/0123914 A1 relates to measuring the curing behavior of plastics.

The object of the present invention is based on the task of providing a method for in-line measuring of the solidification, contraction and wall separation behaviors of confectionary/chocolate products that are poured and solidify in molds; the goal is to be able to ascertain the optimal demolding time for products that are created by pouring and hardening in molds and that are made of the above materials.

Furthermore, another object of the present invention envisions providing an advantageous device for the implementation of the method.

The object regarding providing a method is achieved by the characteristics as set forth in patent claim 1.

To date it has not been possible to arrive at an in-line determination of the solidification and, consequent thereto, product separation processes during cooling based on product-typical volume contraction during the cooling phase of mold-created confectionary/chocolate products. As a consequence for the manufacturers of such products, this means (i) excessive dwelling times during the cooling/solidification process which results in only partially utilized production capacities, or (ii) abbreviated dwelling times that result in partial product adhesions to the walls of the mold and thereby poor demolding properties accompanied by product damage (surface errors) and mold contamination. The invention provides that the solidification and wall separation processes are measured in-line during the cooling/solidification steps of the production of poured confectionary/chocolate products in order to deliver clear criteria for the optimized adjustment of cooling/solidification parameters, such as e.g. the cooling temperature, cooling air speed, dwelling time in the cooling line (e.g. determined via the speed of the conveyor belt). Such information is transmitted telemetrically to a control/rule computer or an external computer, or it is read by a computer after a run through a mold that is equipped with the corresponding technical measuring and electronics instrumentation. The product quality can be optimized based on the in-line measurement technique according to the invention.

The method according to the invention thus allows for non-invasive measuring of the solidification properties and the specific separation time of masses that have been poured into molds after subjecting them to a suitable process, e.g. a cooling process in order to achieve solidification/hardening. Based on the characteristic progression of the signal curve, it is possible to establish precisely the level of solidification and the separation of the hardened mass from the walls of the mold.

Using a signal generator, for example, an ultrasonic transmitter is excited and, based on the transmitted vibration signal that is received by the receiver, the amplitude attenuation and the phase shift of the empty mold at room temperature are established. A mold-specific calibration signal has thus been saved. Now the mold can be used for pouring product.

The transmitted ultrasonic waves propagate in the material of the mold and, if present, in the mass that was poured into the mold, for example chocolate; the waves are detected by the receiver. During this process, energy losses occur due to the absorption of energy, i.e. dissipative conversion of vibration energy to molecular friction and vibration with excited material, resulting in a weakened receiver amplitude signal and phase shift thereof. The higher the viscosity of the material which is caused to vibrate the more intense is the dissipative amplitude attenuation and phase shift. The higher the elasticity of the material the less marked are the amplitude attenuation and phase shift. Aside from the material type of the mold, the product that was filled into the mold and that adheres to the walls and is made to vibrate also influences the attenuation-dependent change of the vibration. Thus, the latter becomes dependent as well of the type of material that is filled into the mold, the material's viscosity as well as the temperature and solidity of the adhesive connection between the material of the mold and the poured-in material. If there is a solid adhesive connection between the material of the wall of the mold and the poured-in material and if these two materials have a comparable sound velocity, it is possible for the ultrasonic wave to cross over from the material of the wall of the mold to the poured-in material without great energy loss. But if there are major differences between, in terms of the sound velocity, two neighboring material phases, as is the case, for example, if an, even if very narrow, air gap forms between the wall of the mold and poured-in material after the poured-in material has separated from the wall, the reflection of the ultrasonic waves at the phase border areas is intensified. This causes the poured-in material to be included in the vibration only to a reduced degree.

During the cooling of chocolate and/or of chocolate-type masses as the material that is poured in the mold and typical plastic molds (Macrolon) as wall material, with the start of the solidifying crystallization of the chocolate, a ca. 1-3% volume contraction occurs. Said contraction ultimately results in the separation of the poured-in material from the wall of the mold. This creates a narrow air gap between the wall of the mold and the chocolate where the ultrasonic wave is partially reflected, leading to a reduction of the amplitude attenuation; i.e., the amplitude climbs for the received signal due to a reduced attenuation. Since the separation from the wall of the mold starts in a localized fashion and progresses until the separation is complete, presumably the amplitude signal increases more or less continuously.

During the cooling process the chocolate passes through different "stages of consistency" ranging from liquid via pasty to solid. Since the attenuation of the ultrasonic signal—as described previously—depends on viscosity, temperature and adhesive connection between the poured-in material and the material of the mold, the received sound signal represents a superimposition of all dependencies. Surprisingly, it was found, however, that, as soon as the chocolate separates from the wall, the related reduction effect of the attenuation of the amplitude clearly dominates the other influences. Thus, based on the maximum value of the received amplitude signal, the relevant point in time when the separation of the poured-in mass from the wall of the mold is complete can be clearly delimited. This point in time marks the required cooling length to achieve an optimally glowing surface result. This was confirmed by demolding tests with chocolate bars implemented at various points during the process.

After the amplitude maximum value that was determined in this way (=attenuation minimum), the continued cooling process of the material of the mold causes a steady reduction of the amplitude. If "interim maximum values" occur during the continuing separation process of the poured-in mass from the wall of the mold, usually there is no continuity regarding the signal following such an interim maximum; i.e., then follows a discontinuous curve progression of the amplitude function over time due to the continuing partial separation from the wall of the mold. But if the subsequent signal after a maximum value shows a continuous progression characteristic, e.g., further continuing decrease due to the continuing cooling, this is—as could be shown—a sufficient measure for the fact that the respective amplitude maximum value represents the point of complete separation.

The method according to the invention thus utilizes a measuring device according to the invention that is installed in the mold in such a way that it performs in-line monitoring of the solidification/hardening behaviors of the mass that was poured into the mold during the cooling process and transmits the corresponding data to a process computer. This way the optimum point in time for demolding is exactly determined, while achieving the minimum process time as well as optimal product quality by providing a controlling process that is coupled to a process computer that takes into account adjusting orders of magnitude such as: cooling temperature, cooling air speed and conveyor belt speed.

Further advantageous embodied examples according to the invention are specified in patent claims 2 to 5.

The object of providing the corresponding device is resolved by the characteristics as captioned in patent claim 6.

This device can be easily achieved with simple means and provides reliable measuring results. With these simple means it is possible to substantially lower the investment that is otherwise customary for commonly used production lines relative to the state of the art; plus, construction dimensions can be drastically reduced, such as the length of the cooling tunnel, etc.

The patent claims 7 to 20 describe embodiments according to the invention of the device as specified in claim 6.

Figure 2:
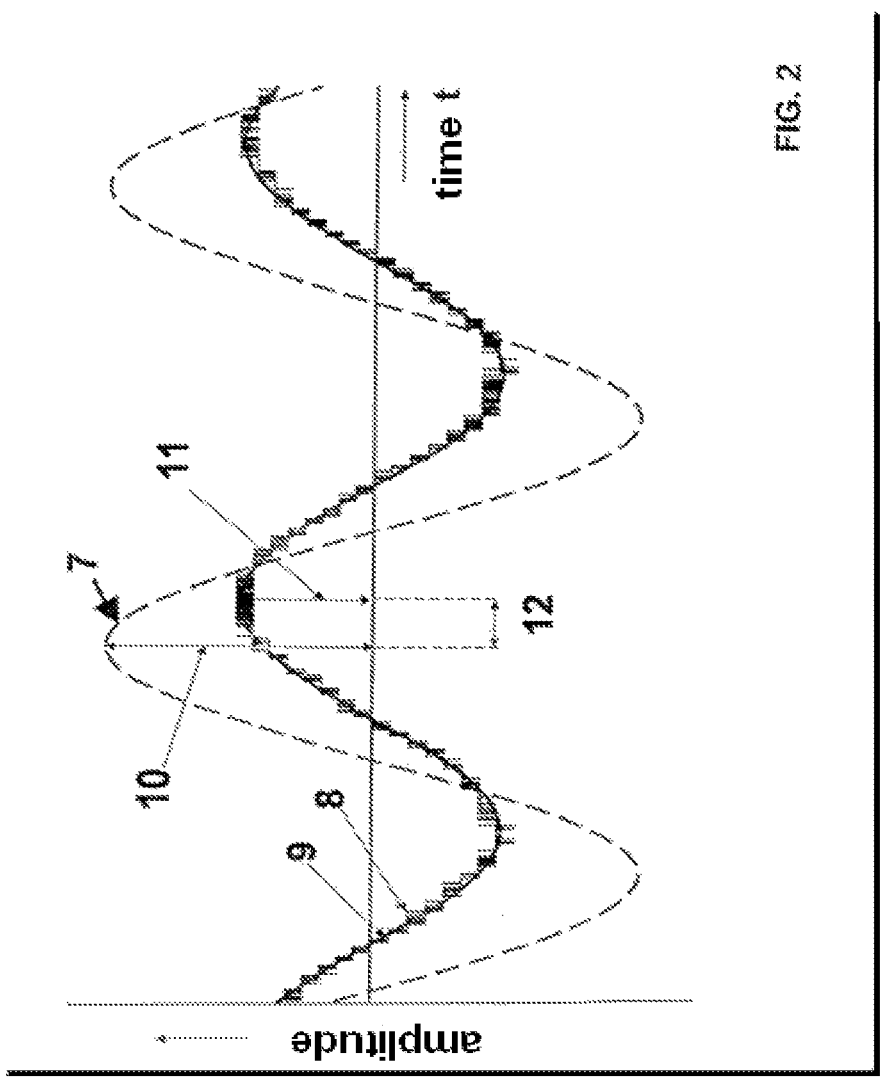
Figure 3:
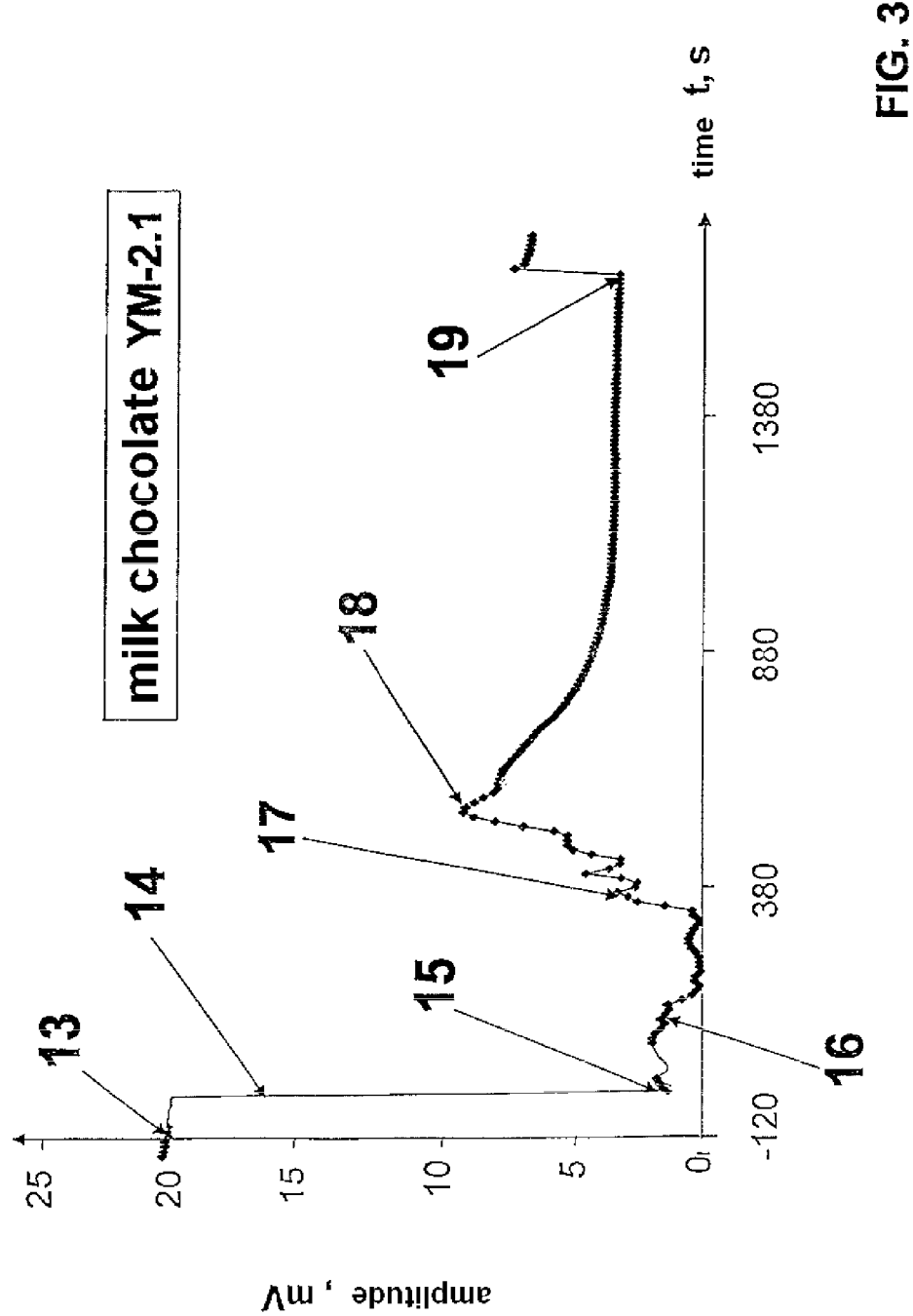
Figure 4:
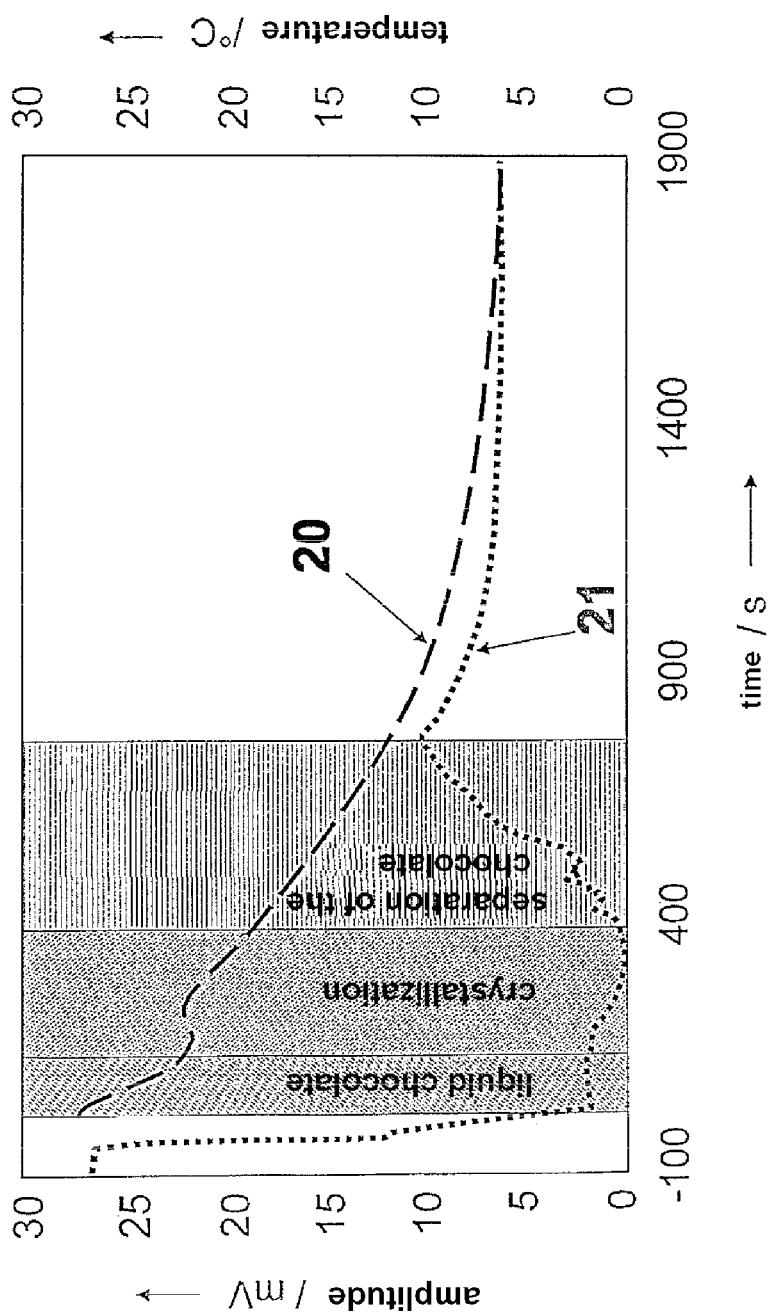
Figure 5:
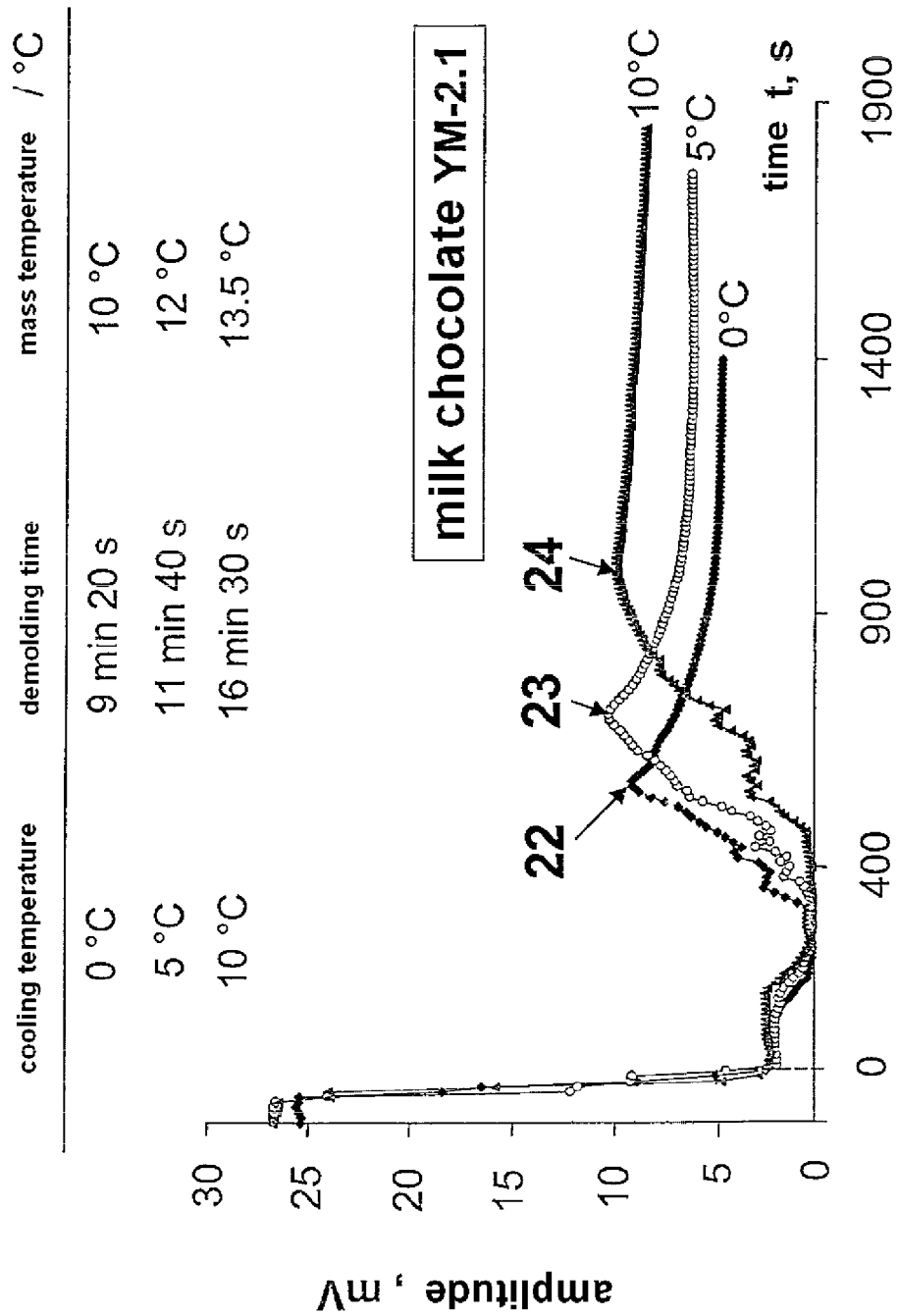

The drawings show exemplary depictions of the invention. Shown are in:

FIG. 1 a bottom view of a wall of a mold;

FIG. 2 an amplitude time diagram with ultrasonic transmission signal and ultrasonic receiver signal;

FIG. 3 an amplitude time diagram for milk chocolate;

FIG. 4 an amplitude time diagram with the temperature progression in chocolate that is to be solidified in comparison with the amplitude progression as a function of time; and FIG. 5 an amplitude time diagram with different cooling temperatures for milk chocolate.

a) GEOMETRY/APPARATUS

FIG. 1

The measuring device comprises two ultrasound sensors (transmitter 1 and receiver 2) that are connected to the wall of the mold that is to be filled in such a way that no direct contact can occur between the sensor and the poured-in material. This means normally the use of a rear-wall installation. The distance between sender and receiver (sensors) is preferably selected in such a way that a length covered by poured-in material located between the two sensors is a long as possible.

Disposed on the rear of the "measuring mold" are furthermore a microcomputer/microprocessor 6 in a waterproof housing and a battery power supply 5 that is fixedly connected to the mold and that supplies voltage. Envisioned for the purpose of measuring the temperature of the mass at the wall of the mold are, additionally, integrated thermocouples 4, which are installed from the rear of the mold, possibly with contact to the poured-in mass.

b) FUNCTION

FIGS. 2, 3

The ultrasonic sender 1 is excited by the signal generator, and the amplitude attenuation and the phase shift of the empty mold at room temperature are determined based on the vibration signal that is transmitted and received by the receiver 2. A mold-specific calibration signal has thereby been saved. Afterwards the mold can be used in the production process.

The transmitted ultrasonic waves 7 propagate in the mold material and possibly in the mass that has been poured into the mold (e.g. chocolate), and they are detected by the receiver 2. During this step energy is lost due to energy absorption; i.e., dissipative conversion of the vibration energy to molecular friction in the material that has been excited to vibrate, which causes a weakening of the receiver amplitude signals 8, 9 (amplitude attenuation 10, 11) and phase shift 12. The more viscous the material that is caused to vibrate the more pronounced are the dissipative amplitude attenuation and phase shift. The more elastic the material the less pronounced are, correspondingly, the amplitude attenuation and phase shift. Aside from the material type of the mold, the material that is also brought to vibrate and adheres to the wall of the mold influences the change of the vibration that is caused by the attenuation. Consequently, the vibration is also dependent on the type of the poured-in material, its viscosity and temperature as well as the solidity of the adhesive connection between the material of the mold and the poured-in material. If a solid adhesive connection exists between the material of the mold and the poured-in material with both of these materials having a comparable sound velocity, the ultrasonic wave can cross over from the material of the wall of the mold to the poured-in material with a low energy loss. But if there are large differences in the sound velocity of adjacent material phases, as is the case, for example, if an air gap forms after the separation from the wall, or be it a minimal air gap, between the wall of the mold and the poured-in material, the reflection of the ultrasonic waves at the location of the phase border area is intensified. This causes the poured-in material to be included in the vibration only to a reduced degree.

During the cooling of the chocolate and/or chocolate-type masses as poured-in material and the typical plastic molds (Macrolon) as wall material, with the start of the solidifying crystallization of the chocolate, there occurs a ca. 1-3% volume contraction. This contraction ultimately results in the separation of the pouring material from the wall of the mold creating a narrow air gap between the wall of the mold and the chocolate where the ultrasonic wave is partially reflected, thus resulting in a reduction of the amplitude attenuation; i.e., the amplitude for the received signal increases because of reduced attenuation. Since the separation from the wall of the mold starts locally and progresses from there until the separation is complete, presumably a more or less continual increase of the received amplitude signal over this time period must be expected.

During the cooling process the chocolate passes through various "stages of consistency" ranging from liquid via pasty to solid. Due to the fact that the attenuation of the ultrasonic signal is—as described previously—dependent on viscosity, temperature and adhesive connection between the poured-in material and the material of the mold, the received sonic signal represents a superimposition of all of these dependencies. Surprisingly, it was found, however, that as soon as the chocolate separates from the wall, the related reduction effect of the attenuation of the amplitude clearly dominates the other influences. Thus, based on the maximum value of the received amplitude signal (FIG. 3, 18), the relevant point in time when the separation of the poured-in mass from the wall of the mold is complete can be clearly delimited. This point in time marks the required cooling length to achieve an optimally glowing surface result. This was confirmed by demolding tests with chocolate bars implemented at various points in time.

After the amplitude maximum value that was determined in this way (=attenuation minimum) the continued cooling process of the material of the mold causes a steady reduction of the amplitude (FIG. 3, 19). If "interim maximum values" (FIG. 3, 17) occur during the continuing separation process of the poured-in mass from the wall of the mold, usually there is no continuity regarding the signal following such an interim maximum; i.e., then follows a discontinuous curve progression of the amplitude function over time due to the continuing partial separation from the wall of the mold. But if the subsequent signal after a maximum value shows a continuous progression characteristic, e.g. further continuing decrease due to the continuing cooling, this is—as could be shown—a sufficient measure for the fact that the respective amplitude maximum value represents the point of complete separation.

c) MEASURING RESULTS

FIGS. 3, 4, 5

FIGS. 3 to 5 show time-related amplitude progressions (receiver) as a function of the process time for the Macrolon bar molds after pre-crystallization (tempering) for poured-out milk chocolate (YM-2.1). FIG. 4 shows the temperature progression in the poured-in mass, additionally integrated. FIG. 5 demonstrates the influence of different cooling temperatures (cooling air flow).

A receiver amplitude of ca. 20 mV (FIG. 3, 13) is seen for the empty mold at room temperature conditions, which decreases during the filling process with milk chocolate mass at ca. 28° C. until complete filling of the mold to ca. 1.7 mV (FIG. 3, 15). The cooling that begins subsequently (in FIG. 3 at 10° C. cooling temperature) causes a progression of the solidifying crystallization and thereby an increase of the viscosity of the mass with subsequently further intensified amplitude attenuation (to ca. 0.023 mV amplitude signal). Ca. 380 seconds after the beginning of cooling, the mass in the mold has solidified for the most part; and because of the mass contraction that is associated therewith, the separation from the wall of the mold starts. This causes the continual, usually not evenly progressing, air gap formation between the wall of the mold and the mass and thereby a non-continually decreasing amplitude attenuation (FIG. 3, 17). A maximum of the amplitude at ca. 550 s with subsequently visibly improved, steadily continuing decrease corresponds to a complete mass separation from the wall of the mold (FIG. 3, 18), and thereby the ideal point in time for demolding. The amplitude decrease after passing this maximum value in the progression of the amplitude can be attributed to the further cooling of the system. This is demonstrated in FIG. 4 by the additional temperature progression in the cooling mass (FIG. 4, 20), synchronous relative to the amplitude progression. The corresponding temperature measurement was done in the mass by an integrated thermocouple (see FIG. 1, 4).

FIG. 5 impressively shows that a cooling temperature that is varied on a broad scale (here between 0 and 10° C.) creates in terms of the characteristic molds same-type, time-related amplitude progressions based upon which the respective maximum values after the start of cooling can be clearly ascertained for optimal demolding times at the corresponding cooling temperatures (FIG. 5, 22, 23, 24, see also the table FIG. 5). Using a wireless connection, the time-related progressions of the amplitude and temperature functions can be transmitted directly from the process and virtually without delay to a process computer or an external computer. In the alternative, a temporary save on an electronic component is also possible; after the removal of the measuring mold from the process (after demolding) the saved data can be read by a computer via cable connection.

The characteristics that are disclosed in the patent claims and in the description as well as the drawings can be essential for the realization of the invention both individually and in combination.

REFERENCE SYMBOLS

1 Ultrasonic transmitter
2 Ultrasonic receiver
3 Individual mold
4 Thermocouple (temperature measurement)
5 Energy source (battery or accumulator)
6 Micro processor, signal processing, storage, (radio) wireless/telemetry connection
7 Ultrasonic transmission signal
8 Ultrasonic receiver signal
9 Sinus curve for receiver signal
10 Ultrasonic transmission signal—amplitude
11 Ultrasonic receiver signal—amplitude
12 Phase shift between transmission and receiving signals
13 Ultrasonic receiver signal—amplitude (empty mold, room temperature)
14 Ultrasonic receiver signal—amplitude (when filling the mold)
15 Ultrasonic receiver signal—amplitude (filled mold, start of cooling)
16 Ultrasonic receiver signal—amplitude (viscosity increase due to crystallization)
17 Ultrasonic receiver signal—amplitude (partial separation from the wall of the mold)
18 Ultrasonic receiver signal—amplitude (complete separation from the wall of the mold)
19 Ultrasonic receiver signal—amplitude (emptying the mold, demolding)
20 Temperature progression of the solidifying mass (here: chocolate) as a function of time
21 Amplitude progression as a function of time
22 Amplitude progression as a function of time at 0° C. cooling temperature
23 Amplitude progression as a function of time at 5° C. cooling temperature
24 Amplitude progression as a function of time at 10° C. cooling temperature

LITERATURE

/1/ Rehm, G., Waubke, N. V., Neisecke, J.: *Ultraschall-Untersuchungsmethoden in der Baupraxis—Literatursichtung*. Berichte aus der Baupraxis [lit.: Ultrasound testing methods in construction practice—a literature review. Reports from construction practice] 84 (1973), pp. 3-23.

/2/ Teodoru, G.: *Zerstörungsfreie Betonprüfung: insbesondere Anwendung von Ultraschall; kritische Betrachtungen*. [lit.: Destruction-free concrete testing: especially application of ultrasound; critical considerations], Düsseldorf: Beton-Verl., 1989.

/3/ Popovics, J. S., Rose, J. L: *A survey of developments in ultrasonic NDE of concrete*. IEEE Trans, on Ultras., Ferroelectr. and Freq. Contr. 41 (1994), Nr. 1, S. 140-143.

/4/ Berger, R. (2000). *Moderne bildgebende Verfahren der medizinischen Diagnostik-ein Weg zu interessanterem Physikunterricht*. [lit.: Modern imaging processes in medical diagnostics—a path for a more interesting study of physics] Diss. University of Munich. Berlin: Logos Verlag /5/ Baker D. W. et al. (1978) Doppler principles and techniques; Ed. Fry, F. T., Amsterdam, 219-254.

/6/ Ouriev, B., and Windhab, E.-(2003). "Transient Flow of Highly Concentrated Suspensions Investigated Using the Ultrasound Velocity Profiler-Pressure Difference Method." *Measurement Science & Technology,* 14(11), 1963-1972.

/7/ Birkhofer, B., Jeelani, S. A. K., Ouriev, B., and Windhab, E. J. (2006). "In-line characterization and rheometry of concentrated suspensions using ultrasound." *Ultrasound 06*, Leeds, UK, February 8-10.

/8/ FR 2 656 425 A1

/9/ R. Saggin, et. al., "Measurement of solid fat content by ultrasonic reflectance in model systems and chocolate," Food Research International 35 (2002), pp. 999-1005

/10/ US 2006/0123914 A1

The invention claimed is:

1. A method for in-line measuring of the solidification, contraction and wall separation behaviors of confectionary/chocolate products that are poured into molds during their production using several ultrasonic sensors including a transmitter and a receiver, wherein no direct sensor contact exists with the poured-in material, the method comprising:
    establishing the amplitude attenuation and the phase shift of the empty mold at room temperature based on the transmitted vibration signal that is received by the respective receiver;
    saving a mold-specific calibration signal in a computer using the respective mold for the pouring-in process of confectionary/chocolate products;
    detecting the ultrasonic waves that propagate through the material of the mold and the poured-in confectionary/chocolate products by the respective receiver;
    delimiting, based on the dissipative amplitude attenuation and phase shift from the maximum value of the received amplitude signal, the relevant point in time for the complete separation of the poured-in mass from the wall of the mold; and then
    determining the point in time for demolding of the confectionary/chocolate products based on the subsequent visibly improved continually progressing decrease of the amplitude for a complete separation of the mass from the wall of the mold.

2. The method as claimed in claim 1, wherein delimiting, based on the dissipative amplitude attenuation and phase shift from the maximum value of the received amplitude signal, the relevant point in time for the complete separation of the poured-in mass from the wall of the mold comprises determining the relevant point in time of the complete separation of the poured-in mass from the wall of the mold based on the maximum value of the received amplitude signal with a subsequent steady decrease of the amplitude.

3. The method as claimed in claim 1, further comprising transmitting the time-related progressions of the amplitude and temperature functions via a wireless connection from the process, virtually without delay and directly, to a process computer or external computer.

4. The method as claimed in claim 1, further comprising temporarily saving the time-related progressions of the amplitude and temperature functions of the process onto an electronic component, and computer reading the data via a cable connection after the removal of the measuring-mold from the process after demolding.

5. The method as claimed in claim 1, further comprising detecting data that in-line regarding the solidification/hardening behaviors of the confectionary/chocolate masses, the wall separation behavior and the point in time that the wall separation is complete, and using the detected data for controlling or regulating the process parameters that influence the solidification process in order to achieve minimum dwelling times within the process and/or for the optimization of the quality of the product properties.

6. A device for implementing the method as claimed in claim 1, wherein, in the wall that delimits the solidifying mass and the vibration behavior of which is being measured at least one ultrasonic transmitter is disposed for the excitation of the vibration and at least one ultrasonic receiver for receiving the partially attenuated vibration that is attenuated by the material of the wall and the contacting confectionary/chocolate masses.

7. The device as claimed in claim 6, wherein the exciting vibration frequency of the respective ultrasonic transmitter is harmonized with the resonant frequency of the wall that delimits the solidifying confectionary/chocolate masses.

8. The device as claimed in claim 6, wherein the distance between the respective ultrasonic transmitter and the associated receiver is between one and one hundred centimeters.

9. The device as claimed in claim 6, wherein the mechanical vibration that is applied to the delimiting wall is in the frequency range of 100 Hz to 100 kHz, preferably in a range of 10-70 kHz, preferably in the form of a periodical, sinus-shaped signal.

10. The device as claimed in claim 6, wherein the frequency and amplitude of the vibrations that are applied to the wall of the mold are adjustable.

11. The device as claimed in claim 6, wherein the vibratory pulses that are applied to the wall of the mold are adjustable or fixable regarding pulse length, frequency and duration.

12. The device as claimed in claim 6, wherein a mechanical vibration donor and vibration receiver are connected to the wall, for example, with a rear and/or base rear side of the mold and are therefore not in contact with the product.

13. The device as claimed in claim 12, wherein the vibration donor and vibration sensor are disposed at a distance relative to each other in an arrangement that corresponds to the characteristic extended length of a molded product piece.

14. The device as claimed in claim 6, wherein a recording/save of the time-related progression of the respectively detected vibration response occurs, and wherein this recording can occur in an electronic storage unit, and wherein, based on the analysis of the time-related amplitude progression, it is possible to detect, based on the amplitude maximum value with a subsequently continuous decrease of the amplitude signal, the point in time for demolding the confectionary/chocolate products.

15. The device as claimed in claim 6, wherein a temperature measurement is taken via thermocouples at different location of the molds and/or mold base surfaces and that these temperature data can also be recorded as a function of the time via the storage unit.

16. The device as claimed in claim 6, wherein the electronics unit that records the time-related progressions of the vibration response and the temperature with the wall, are connected in the rear.

17. The device as claimed in claim 6, wherein the time-related progressions of the vibration response and the temperature progression can be read or determined from the electronic storage component by a computer (laptop).

18. as claimed in claim 6, wherein the time-related progressions of the vibration response and the temperature progression can be transmitted from the electronic storage component to a process computer or an external computer (laptop) by way of a wireless radio transmission.

19. The device as claimed in claim 6, wherein the automatic detection of an amplitude maximum value of the vibration response after the start of the solidification with subsequently continuous amplitude progression occurs on the basis of the time-related progressions of the vibration response and the temperature, which are detected in-line and can be transmitted without contact via a radio module.

20. The device as claimed in claim 6, wherein the ultrasonic transmitter, ultrasonic receiver, thermocouples, microprocessors, energy source (battery) and the electronic unit for the wireless data transmission or data storage are installed at the bottom of the wall, in the rear of the mold.

* * * * *